US008227609B2

(12) United States Patent
Weigl et al.

(10) Patent No.: US 8,227,609 B2
(45) Date of Patent: Jul. 24, 2012

(54) PROCESS FOR PURIFYING NOROXYMORPHONE COMPOUNDS

(75) Inventors: Ulrich Weigl, Hilzingen (DE); Ulf Kötz, Tengen (DE); Ilia Freifeld, Frankfurt am Main (DE)

(73) Assignee: CILAG AG, Schaffhausen (CH)

( * ) Notice: Subject to any disclaimer, the term of this patent is extended or adjusted under 35 U.S.C. 154(b) by 539 days.

(21) Appl. No.: 11/815,784

(22) PCT Filed: Feb. 9, 2006

(86) PCT No.: PCT/CH2006/000087
§ 371 (c)(1), (2), (4) Date: Nov. 9, 2007

(87) PCT Pub. No.: WO2006/084412
PCT Pub. Date: Aug. 17, 2006

(65) Prior Publication Data
US 2009/0270624 A1    Oct. 29, 2009

(30) Foreign Application Priority Data

Feb. 11, 2005    (WO) ................ PCT/CH2005/000076

(51) Int. Cl.
*C07D 221/22*        (2006.01)
(52) U.S. Cl. ........................................ 546/74
(58) Field of Classification Search ..................... 546/74
See application file for complete search history.

(56) References Cited

FOREIGN PATENT DOCUMENTS

| DE | 2727805 A1 | 1/1979 |
| EP | 0158476 A1 | 10/1985 |
| WO | WO 91/05768 A1 | 1/1991 |
| WO | WO 95/32973 A1 | 12/1995 |
| WO | WO 99/02529 A1 | 1/1999 |

*Primary Examiner* — Nizal Chandrakumar
(74) *Attorney, Agent, or Firm* — Hammer & Associates, P.C.

(57) ABSTRACT

A process for purifying plant extracts which consist essentially of noroxymorphone compounds and which comprise, as impurities, α,β-unsaturated noroxymorphone compounds, by (a) converting the plant extract or the product of a subsequent stage in the synthesis of a selected noroxymorphone compound in a reaction which converts the hydroxyl groups present in the mixture to leaving groups of the formula —$OR_2$ in which $R_2$ is the introduced radical of the leaving group, (b) these leaving groups are optionally detached again, then (c) the resulting mixture is subjected to a selective hydrogenation, so that a saturated bond is formed in the α,β-position of the unsaturated noroxymorphone compounds and any remaining leaving groups are each converted to a hydroxyl group and then optionally (d) the pure noroxymorphone compound is isolated; processing of the noroxymorphone purified in this way to naltrexone or naloxone or a salt of these compounds or a quaternary derivative of these compounds; pharmaceutical formulations comprising such a compound.

18 Claims, No Drawings

PROCESS FOR PURIFYING NOROXYMORPHONE COMPOUNDS

The present invention relates to a process for purifying noroxymorphone compounds. The present invention also relates to a process for preparing pure noroxymorphone compounds, especially naltrexone and naloxone, especially pure naltrexone.

Noroxymorphone is designated chemically as 7,8-dihydro-14-hydroxynormorphinone or as α,β-dihydro-14-hydroxynormorphinone and corresponds to the formula

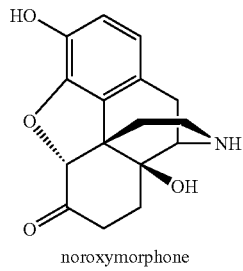

noroxymorphone

Noroxymorphone compounds and their preparation are described, for example, in DE 272 78 05. A selected derivative of noroxymorphone is the compound known as naltrexone, which corresponds to the following chemical formula:

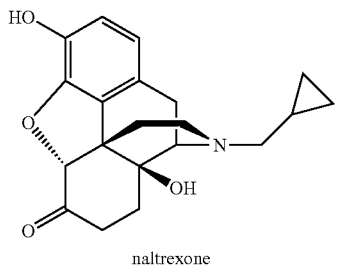

naltrexone

Naltrexone and its derivatives and salts, for example naltrexone hydrochloride, N-methylnaltrexone bromide (methylnaltrexone) or naltrexone methobromide, are known pharmaceutically active compounds which are used in particular to reduce psychological dependence in the event of drug abuse. Naltrexone methobromide is used, for example, as an antagonist of the mu receptor, in order to prevent side effects of narcotics. Naloxone (CAS No. 465-65-5) is substituted by an allyl radical on the nitrogen atom and is pharmaceutically active in a similar manner. Being morphine derivatives, these compounds are synthesized from precursors which stem from the class of the morphine-like alkaloids of the corn poppy. Since the total synthesis of this complicated class of natural substances is complex, the starting materials for the synthesis of noroxymorphone compounds are obtained from plant sources by means of extraction. However, the extraction of plants, in the present case of poppy, does not selectively afford only one individual compound, but rather a mixture of numerous structurally similar compounds. Many of these extracted compounds are toxic or give rise to toxic compounds in the course of further chemical conversion, for example in the further synthesis to give oxymorphone, noroxymorphone and naltrexone. Particularly problematic impurities have been found to be α,β-unsaturated compounds, for example the compound of the formulae (Ia), (Ib) and (Ic).

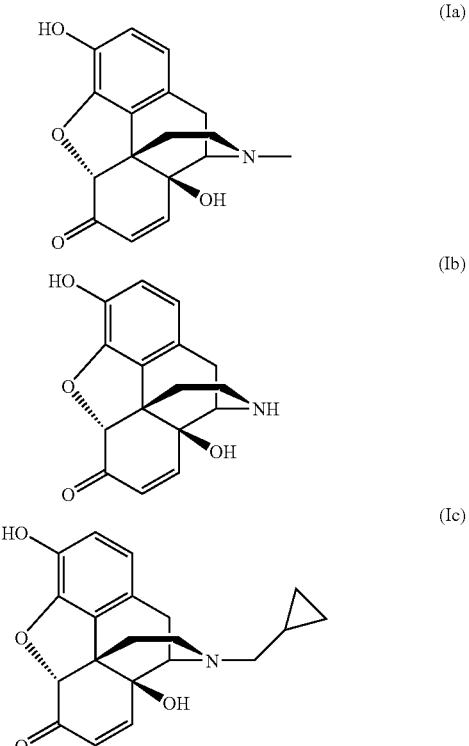

It is equally possible for potential precursors of these compounds, for example corresponding α-substituted and/or β-substituted alcohols to be present as an impurity in the plant extraction mixture, which can in turn form α,β-unsaturated compounds, for example the compound of the formulae (Ia), (Ib) and (Ic). In addition, further α,β-unsaturated toxic compounds can be formed in the preparation of naltrexone starting from the plant extracts mentioned, and such compounds may be mutagenic, teratogenic and/or carcinogenic. The limiting values for these compounds in naltrexone and naltrexone derivatives have therefore been lowered to 100 ppm, and in some cases to 10 ppm. However, such a specification can generally hardly be fulfilled for products which are synthesized starting from raw materials extracted from plant sources by known processes.

It has now been found that it is possible to comply with or to go below the limiting value of 10 ppm mentioned for the aforementioned α,β-unsaturated compounds when the plant extract which, in addition to the noroxymorphone compound, comprises the corresponding α,β-unsaturated compound and further impurities, or the product of a subsequent stage in the synthesis of a selected noroxymorphone compound, (a) is subjected to a reaction by which the hydroxyl groups present in the mixture are converted to leaving groups, (b) these leaving groups are optionally removed again and then (c) the resulting mixture is subjected to a selective hydrogenation.

The workup of step (a) and of step (b) including a possible isolation of the reaction products is preferably carried out in nonaqueous medium, preferably also in nonalcoholic medium. Preference is given to removing the leaving groups before the hydrogenation. The hydrogenation, i.e. step (c) can be carried out in the presence of aprotic solvents and, under mild conditions, also in the presence of protic solvents such as water and alcohols. After the hydrogenation, any leaving groups still present can additionally be removed by means of hydrolysis.

As a result of this conversion of the hydroxyl groups present in the mixture to leaving groups [step (a)] and optional subsequent removal of these leaving groups [step (b)], all critical impurities which are present in the starting materials typically in the order of magnitude of about 1000 ppm are removed in the hydrogenation [step (c)] to such an extent that they are no longer detectable analytically by means of HPLC.

It is particularly surprising that, as a result of the inventive pretreatment of the crude product, i.e. of the plant extract, the hydrogenation acts so selectively that all critical by-products are removed virtually entirely, while the desired hydroxyl groups are formed again from the leaving groups in the noroxymorphone compounds without the keto group present being hydrogenated or removed or converted to a hydroxyl group. Such high purities cannot be achieved by simple hydrogenation of the crude mixture. It is suspected that potential precursors of the noroxymorphone compound, for example corresponding α-substituted and/or β-substituted alcohols, which are present as an impurity in the plant extraction mixture, are altered by the inventive reactions in step (a) or steps (a) and (b) to such an extent that they or subsequent products (for example elimination products) from these reactions are converted to methylene groups by the hydrogenation in step (c). However, the present invention is not tied to this explanation.

According to the invention, it is also possible, for example in the preparation of noroxymorphone or in its further processing to naltrexone or naloxone and salts thereof, for either the starting mixture or any intermediate or else the end product, i.e. naltrexone or naloxone, preferably the starting mixture or an intermediate, to be subjected to the inventive treatment in step (a) and step (b) and then hydrogenated.

The starting mixture consists generally of oxymorphone

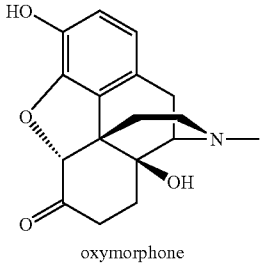

oxymorphone which has been prepared from the natural substances of thebaine or oripavine extracted from the plant materials.

The present invention relates to a process for purifying plant extracts which consist essentially of noroxymorphone compounds of the formula (II) and which comprise, as impurities, α,β-unsaturated noroxymorphone compounds and further contaminating noroxymorphone compounds:

(II)

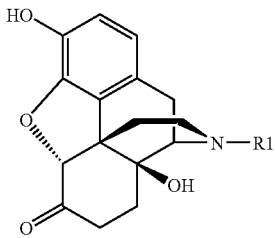

in which $R_1$ is hydrogen, optionally phenyl- or chlorine-substituted $(C_1-C_8)$-alkyl, $(C_2-C_4)$-alkenyl or a detachable leaving group known per se, characterized in that (a) the plant extract or the product of a subsequent stage in the synthesis of a selected noroxymorphone compound is converted in a reaction which converts the hydroxyl groups present in the mixture to leaving groups of the formula —$OR_2$ in which $R_2$ is the introduced radical of the leaving group, (b) these leaving groups are optionally detached again and then (c) the resulting mixture is subjected to a selective hydrogenation, so that a saturated bond is formed in the α,β-position of the contaminated noroxymorphone compounds and any remaining leaving groups are each converted to a hydroxyl group and then, optionally, (d) the pure noroxymorphone compound is isolated.

The present invention also relates to the oxymorphone compounds of the formula (II) purified by the process according to the invention or to a mixture of such compounds, and to pharmaceutical formulations comprising such a compound.

$R_1$ is preferably hydrogen, $(C_1-C_8)$-alkyl, $(C_2-C_4)$-alkenyl or a leaving group; preferably $(C_1-C_6)$-alkyl, allyl or hydrogen, preferably $(C_1-C_6)$-alkyl or hydrogen.

$R_1$ as the leaving group is preferably $(C_1-C_4)$-alkyloxycarbonyl [$(C_1-C_8)$-alkyl-O—C(O)—] or phenyloxycarbonyl [phenyl-O—C(O)—], preferably ethyloxycarbonyl, isobutyloxycarbonyl, or tert-butyloxycarbonyl (Boc), cyclohexyloxycarbonyl, preferably ethyloxycarbonyl or tert-butyloxycarbonyl (Boc). The procedure for the introduction of the radical is known per se, by reacting the compound of the general formula (II) (in which $R_1$ is hydrogen or a replaceable radical), for example with Boc anhydride (Boc-O-Boc) {[$(CH_3)_3$C—O—C(O)]$_2$—O} or with Boc carbamate [$(CH_3)_3$C—O—C(O)—N$(C_{1-4}$-alkyl)$_2$]. Such radicals and their introduction on nitrogen atoms are known per se.

When the compound of the formula (II) is an end product, $R_1$ therein is preferably methylenecyclopropyl (—$CH_2$—$C_3H_5$) or allyl (—$CH_2$—CH=$CH_2$). Preference is given to hydrogenating a compound or a compound mixture in which $R_1$ is neither methylenecyclopropyl nor allyl and the preferred end product is prepared from the hydrogenated product.

The definition "consisting essentially of noroxymorphone compounds of the formula (II) and which comprise, as impurities, α,β-unsaturated noroxymorphone compounds and further contaminating noroxymorphone compounds" means that the plant extracts as a solid contain a total of about at least 70% by weight, preferably at least 80% by weight and preferably at least about 90% by weight of noroxymorphone compounds, the ratio of the noroxymorphone compounds of the formula (II) to the contaminating noroxymorphone compounds being about in the range from 99.800% by weight to 99.999% by weight of noroxymorphone compounds of the formula (II) to from about 0.200% by weight to 0.001% by weight of contaminating compounds, and all solids present in the extract together adding up to 100% by weight.

In the leaving group of the formula —$OR_2$, —$OR_2$ preferably forms an ester moiety, for example the formyl ester radical [$R_2$=HC(O)—], acetyl ester radical [$R_2$=$CH_3$C(O)—, methylcarbonyl], trichloroacetyl ester radical [$R_2$=$CCl_3$C(O)—], trifluoroacetyl ester radical [$R_2$=$CF_3$C(O)—, trifluoromethylcarbonyl], benzoyl ester radical [$R_2$=$C_6H_5$C(O)—], optionally substituted benzyl ester groups, or esters of sulfonic acids in which $R_2$ is preferably methylsulfonyl, benzylsulfonyl or p-toluenesulfonyl. Alternatively, —$OR_2$ may also form a carbonic ester moiety in which $R_2$ is $(C_1-C_8)$-alkyloxycarbonyl or phenyloxycarbonyl; preferably ethyloxycarbonyl, isobutyloxycarbonyl or tert-butyloxycarbonyl (Boc), cyclohexyloxycarbonyl, preferably ethyloxycarbonyl or tert-butyloxycarbonyl (Boc).

The procedure for the formation of an ester moiety, for example in the case of introduction of acetyl or tert-butyloxycarbonyl (Boc), the procedure is known per se, by reacting the compound of the general formula (II) with acetic anhydride or acetyl chloride or Boc anhydride (Boc-O-Boc) {[(CH$_3$)$_3$C—O—C(O)]$_2$—O}. Acetyl and Boc here represent the other compounds which react in the same way, i.e. compounds in which the methyl or the tert-butyl radical has been replaced by another radical of the same reactivity. The leaving groups are generally removed in the course of the reaction, for example in step (b) or in the hydrogenation, but they can additionally be removed in a manner known per se after the hydrogenation should this be necessary in the particular case.

Preference is given to the introduction of a leaving group, or derivatization, by means of reaction with acid chlorides or acid anhydrides, for example acetic anhydride, acetyl chloride, trifluoroacetic anhydride, methanesulfonyl chloride, methanesulfonyl anhydride, toluenesulfonyl chloride, and related compounds known per se.

The conversion of $R_1$ to a leaving group, if $R_1$ is an alkyl group, is known from the literature for analogous reactions and need not be described further here.

Preference is given to undertaking the further conversion of the reaction mixture obtained in stage (a) in anhydrous medium, preferably also in alcohol-free medium, since the presence of water can result in the formation of impurities, especially alcohols in the α- or β-position, as a result of the addition of water and possibly alcohol to α,β-unsaturated compounds. This is true of the workup of stage (a) and removal of the leaving groups as per stage (b), including a possible isolation of the reaction products. The hydrogenation as per stage (c) can be carried out under mild conditions in aqueous and/or alcoholic solvents. For such treatments in anhydrous and preferably alcohol-free media, aprotic solvents in particular, for example tert-butyl ethers, are suitable.

The leaving group as per stage (a) is introduced by treating the reaction mixture, optionally with heating, with an acylating agent as described above. Subsequent addition of organic solvents, for example MTBE (methyl tert-butyl ether), precipitates out the product.

The procedure for the removal of the leaving groups in stage (b) is preferably to heat the reaction product from stage (a) in nonaqueous solvents, if appropriate over several hours, preferably in aprotic solvents such as THF, dioxane, ethyl acetate, MTBE, DMF, DMSO and the like, optionally with addition of a base such as potassium tert-butoxide or lithium hydroxide in aprotic solvents, for example THF, dioxane or ethyl acetate. The product is preferably subsequently precipitated by adding an aprotic solvent.

Hydrogenation conditions are known per se and are mentioned, for example, in EP 0 158 476, WO 99/02529, WO 95/32973 or WO 91/05768. Preference is given in accordance with the invention to hydrogenation conditions in which, for the hydrogenation in stage (c), elemental hydrogen and/or conditions or compounds which generate elemental hydrogen in situ are used. In this context, preference is given in accordance with the invention to hydrogenation conditions in which, for the hydrogenation in stage (c), elemental hydrogen, cyclohexene and/or cyclohexadiene (which react with release of hydrogen to give benzene) and/or ammonium formate (which decomposes with release of hydrogen to give carbon dioxide and ammonia) as hydrogen sources or in a solvent from the class of the polar organic solvents, optionally with addition of water for solubilization, for example hydrogenation catalysts, are used. Such hydrogenation catalysts are described hereinbelow. Transfer hydrogenations can generally be carried out at standard pressure and are known per se.

Particular preference is given to catalytic hydrogenation using noble metal catalyst in heterogeneous or homogeneous form. Such noble metal catalysts are preferably selected from compounds of the group of transition metals of the periodic table of the elements, especially selected from metals of group VIII of the periodic table, their compounds and complexes, especially of ruthenium (Ru) and osmium (Os), cobalt (Co), rhodium (Rh) and iridium (Ir), nickel (Ni), palladium (Pd) and platinum (Pt). Preference is given to rhodium, palladium and platinum, especially palladium. These metals are used as hydrogenation catalysts in a manner known per se. Thus, it is possible to hydrogenate in heterogeneous form, in which case the catalysts are applied to a support material, preferably to activated carbon or alumina or to other support material known per se, preferably to activated carbon.

Compounds of these metals may preferably also be used as homogeneous catalysts, preferably palladium compounds. Examples of such palladium compounds are Pd(0) compounds known per se, such as tetrakis(triphenylphosphine) palladium and the corresponding complexes having the ligands tri(2-tolyl)phosphine, tri(2-furyl)phosphines, tri(tert-butyl)phosphine, or the bidentate ligands dppm [1,1-bis(diphenylphosphinomethane)], dppe [1,2-bis(diphenylphosphino)ethane] and related compounds, and tris(dibenzylideneacetone)dipalladium-chloroform complex, and Pd(II) compounds, preferably PdCl$_2$, Pd(dppe)Cl$_2$, Pd(OAc)$_2$, Pd(dppe) (OAc)$_2$, π-allyl-Pd complexes, preferably π-allylpalladium chloride dimer. Preference is given to Pd(0) compounds. These compounds, salts and complexes are known per se and have been described in the literature.

The catalysts are used in catalytic amounts, preferably in amounts of 0.0005-0.01% by weight of noble metal, preferably about 0.001-0.005% by weight of noble metal, based on the weight of the crude reactant. The upper limit specified is, though, not critical. Thus, it is also possible to use higher amounts of catalysts, for example equimolar amounts based on the crude product. However, this is generally unnecessary.

The hydrogenation is preferably carried out with hydrogen gas, preferably in an inert solvent, for example in organic acids, preferably glacial acetic acid, formic acid, propionic acid or a mixture of these compounds; in alcohols, preferably methanol, ethanol, isopropyl alcohol, n-butanol or a mixture of these compounds; in nitrites, preferably acetonitrile and/or propionitrile; in ketones, preferably acetone and/or 2-butanone; in esters such as ethyl acetate, in polar aprotic solvents, preferably dimethylformamide (DMF) or dimethylsulfonamide (DMSO), optionally with addition of water. Preference is given to protic solvents, especially methanol, ethanol, isopropyl alcohol, n-butanol, or aprotic polar solvents, preferably acetone, DMF, acetonitrile, optionally in a mixture with 1-99% by weight of water and preferably in the presence of an organic acid, for example acetic acid, trifluoroacetic acid, propionic acid, formic acid, preferably acetic acid, preferably in a concentration of from 0.1% by weight to 99% by weight. The hydrogenation is preferably carried out at a temperature in the range from 0° C. to 150° C., preferably in the range from 20° C. to 100° C., preferably in the range from standard pressure to 100 bar, preferably in the range from standard pressure to 10 bar.

Instead of hydrogen, it is also possible to use compounds which release hydrogen in situ in the reaction, for example transfer hydrogenation with ammonium formate, cyclohexene and/or cyclohexadiene. In this case, the hydrogen is eliminated in a preceding reaction with catalysis of reagent.

The present invention also relates to a process for preparing pure noroxymorphone from plant extracts which consist essentially of noroxymorphone and which comprise contaminating noroxymorphone compounds, characterized in that oxymorphone of the above-specified formula (II), in which $R_1$ is methyl, is initially charged as the plant extract, and (a) the plant extract is reacted in a reaction by which the hydroxyl groups present in the mixture are converted to leaving groups of the formula —$OR_2$ in which $R_2$ is the introduced radical of a leaving group such as those previously described for $R_1$, preferably acyl, preferably acetyl;

(a1) the N-methyl group [corresponding to the definition of $R_1$ of the compound of the formula (II)] is removed and replaced by a leaving group $R_3$ in which $R_3$ is a leaving group such as those previously described for $R_1$, preferably alkyloxycarbonyl, preferably ethyloxycarbonyl or Boc, preferably ethyloxycarbonyl;

(a2) the leaving groups $R_2$ and $R_3$ are optionally removed from the reaction product obtained from stages (a) and (a1);

(b) at least one of the products obtained in stages (a), (a1) and/or (a2), preferably one of the products obtained in stages (a1) or (a2), preferably in stage (a2), is subjected to a selective hydrogenation reaction as described above, and (c) the pure noroxymorphone compound is optionally isolated.

The product obtained in stage (a2) can also be processed further, preferably to give naltrexone or naloxone or a salt of these compounds or a quaternary derivative of these compounds, preferably to the hydrochloride, hydrobromide, methochloride or methobromide, preferably to the corresponding salts or quaternary derivatives of naltrexone.

The selective hydrogenation also removes the leaving groups, but these can optionally be carried out separately in stage (a2) and/or for completion, where necessary, after the hydrogenation.

In stage (a), oxymorphone is preferably esterified by means of acetic anhydride to give methyl tert-butyl ether (MTBE), and worked up under anhydrous conditions and isolated to obtain diacetyloxymorphone ($R_2$=acetyl).

In stage (a1), preference is given to converting by means of ethyl chloroformate in an aprotic solvent, preferably acetonitrile, demethylating under basic conditions, such as with $K_2CO_3$, to isolate an oxymorphone compound in which $R_3$ is ethoxycarbonyl, or the resulting compound being the corresponding diacetyloxymorphone ethoxycarbamate.

In stage (a2), the leaving groups $R_2$ and $R_3$ are removed from the reaction product obtained from stages (a) and (a1). To this end, the reaction product from stage (a) or (a1) is heated in nonaqueous solvents, preferably in aprotic solvents such as THF, dioxane, ethyl acetate, MTBE, DMF, DMSO and the like, if appropriate over several hours, if appropriate with addition of a base such as potassium tert-butoxide or lithium hydroxide, in aprotic solvents, for example THF, dioxane, ethyl acetate. The product is preferably precipitated subsequently by adding an aprotic solvent.

In stage (b), the isolated product, for example diacetyloxymorphone ethoxycarbamate, is preferably dissolved in glacial acetic acid and subjected to a hydrogenation by introducing hydrogen gas under the conditions specified above, catalyzed by palladium on activated carbon. Subsequently, the remaining leaving groups $R_4$ and $R_5$ are eliminated by adding 40% sulfuric acid to the reaction mixture to form noroxymorphone sulfate which can optionally be isolated. Addition of base, for example by adding ammonia solution in ethanol/water, allows the reaction mixture to be neutralized and worked up, and the free noroxymorphone to be isolated. The free noroxymorphone is insoluble in a water/ethanol mixture at a weakly alkaline pH, preferably pH 8-10, and precipitates out as a crystalline solid when the pH is adjusted, which allows it to be filtered off. In the isolated noroxymorphone, no $\alpha,\beta$-unsaturated compounds are detectable by means of HPLC. The noroxymorphone obtained in this way can thus be processed further, preferably to give highly pure naltrexone or naloxone (CAS No. 465-65-5) or to give salts or quaternary derivatives. Preferred salts are the hydrochlorides and hydrobromides. Preferred quaternary derivatives are the compounds naltrexone methobromide (is also referred to as methylnaltrexone) or naloxone methobromide [is also referred to as methylnaloxone (CAS No. 73232-50-5)]. Preference is give to naltrexone hydrochlorides or hydrobromides and naltrexone methobromide.

The noroxymorphone prepared in accordance with the invention can be processed, for example, to give highly pure naltrexone or highly pure naloxone, or to give a highly pure salt or quaternary derivative of these compounds.

In this context, the present invention relates to a process for preparing highly pure salts and quaternary derivatives of naltrexone and naloxone in which the critical olefinic impurities are below the detection limit, preferably salts or naltrexone, by reacting the noroxymorphone starting material with the appropriate alkylating agent, i.e. with cyclopropylmethyl bromide (for naltrexone) or with allyl bromide (for naloxone), and reacting the naltrexone or naloxone product either with an acid, preferably with dilute hydrochloric acid or hydrogen bromide, to give the corresponding salt, in the case described to give the hydrochloride or hydrobromide; or with a further alkylating agent, preferably with methyl bromide, to obtain naltrexone methobromide or naloxone methobromide; characterized in that at least the starting material or a product of stages (a) or (b) obtained as an intermediate or the end product, preferably a product of stages (a) or (b), preferably of stage (b), obtained as an intermediate is subjected to a hydrogenation reaction as described above. The examples which follow illustrate the invention.

EXAMPLE 1

Preparation of Diacetyloxymorphone (DAOM), Introduction of the Leaving Group with Direct Elimination of the Leaving Group 20 g of oxymorphone are suspended in a mixture of 10 g of tert-butyl methyl ether and 21 g of acetic anhydride (3.24 eq.) at room temperature. The reaction solution is heated under reflux for 5 hours. This is followed by cooling and addition of 70 g of tert-butyl methyl ether. The suspension is heated once again to reflux temperature, then cooled to 0-4° C. and stirred further until complete precipitation. The product is filtered off with suction, washed with tert-butyl methyl ether and dried to constant weight at 90° C. under reduced pressure. Yield: 23 g (91% based on the oxymorphone used); HPLC purity: 98%, product contains traces (approx. 1000 ppm) of $\alpha,\beta$-unsaturated compound; 3,8,14-triacetyloxymorphone is not detectable.

EXAMPLE 2

Preparation of Diacetyloxymorphone (DAOM), which Contains Traces of 3,8,14-triacetyloxymorphone; Introduction of a Leaving Group 20 g of oxymorphone are suspended in a mixture of 10 g of tert-butyl methyl ether and 21 g of acetic anhydride (3.24 eq.)

at room temperature. The reaction solution is heated at max. 30-40° C. for 48 hours. This is followed by cooling and addition of 70 g of tert-butyl methyl ether. The mixture is cooled to 0-4° C. and stirred until complete precipitation. The product is filtered off with suction, washed with tert-butyl methyl ether and dried to constant weight at 30° C. under reduced pressure. Yield: 26.8 g (91%, based on the oxymorphone used); HPLC purity: 98%, product contains traces of 3,8,14-triacetyloxymorphone.

EXAMPLE 3

Preparation of Diacetyloxymorphone Carbamate 30 g of diacetyloxymorphone are suspended together with 66 g of ethyl chloroformate (8 eq.) and a heterogeneous base (1 eq. of potassium carbonate) in an organic solvent (74 g of acetonitrile) and heated at elevated temperature (65-68° C.) for several hours (24-28 hours). After the reaction has ended, acetonitrile and ethyl chloroformate are distilled off under reduced pressure. 73 g of acetonitrile are added to the residue. The heterogeneous base ($KHCO_3/K_2CO_3$) is then filtered off at room temperature. The acetonitrile is distilled off under reduced pressure and, for complete precipitation, 60 g of tert-butyl methyl ether are added. After heating to reflux temperature, the mixture is cooled to 0-5° C. and stirred further, then the precipitated solid is filtered off with suction and washed first with tert-butyl methyl ether, then with water. The colorless product is dried under reduced pressure to constant weight at 80° C. According to HPLC, the product contains >1000 ppm of α,β-unsaturated compounds.

Yield: 29 g (86% based on the diacetyloxymorphone used). HPLC purity: >95%.

EXAMPLE 4

Conversion of 3,14-diacetyloxymorphone (DAOM) which Contains Traces of 3,8,14-triacetyloxymorphone to 3,8,14-triacetyloxymorphone-free 3,14-diacetyloxymorphone (DAOM); Elimination of the Leaving Group 20 g of diacetyloxymorphone with traces of 3,8,14-triacetyloxymorphone are suspended in a mixture of 20 g of tert-butyl methyl ether and 3-5 g of acetic acid at room temperature. The reaction solution is heated at 70° C. for 10-15 hours. This is followed by cooling and addition of 70 g of tert-butyl methyl ether. The mixture is cooled to 0-4° C. and stirred until complete precipitation. The product is filtered off with suction, washed with tert-butyl methyl ether and dried to constant weight at 30° C. under reduced pressure. Yield: 15.7 g (91%, based on diacetyloxymorphone used); HPLC purity: 98%, product contains approx. 1000 ppm of α,β-unsaturated compound, 3,8,14-triacetyloxymorphone is not detectable.

EXAMPLE 5

Hydrogenation with Leaving Group 20 g of diacetyloxymorphone with traces of 3,8,14-triacetyloxymorphone, prepared according to example 2, are dissolved in 60 g of glacial acetic acid at room temperature. 0.6 g of water-moist palladium on activated carbon (10% Pd based on the dry substance, water content approx. 50%) is added thereto. Hydrogen gas is then introduced at internal temperature 50-60° C. and 2.7 bar. After the hydrogenation, the catalyst is filtered off and the solution is concentrated to half under reduced pressure. Subsequently, MTBE is added and the mixture is cooled to 0-4° C. The product is filtered off with suction, washed with MTBE and dried at 70° C. under reduced pressure. Purity: 98%; neither α,β-unsaturated compounds nor 3,8,14-triacetyloxymorphone are detectable, yield 85% (diacetyloxymorphone based on diacetyloxymorphone used)

EXAMPLE 6

Hydrogenation with Eliminated Leaving Groups; Preparation of Noroxymorphone 30 g of diacetyloxymorphone carbamate, prepared according to example 3, are dissolved in 60 g of glacial acetic acid at room temperature. 0.6 g of water-moist palladium on activated carbon (10% Pd based on the dry substance, water content approx. 50%) is added thereto. Hydrogen gas is then introduced at internal temperature 50-60° C. and 2.7 bar. After the hydrogenation, the catalyst is filtered off and the solution is concentrated to half under reduced pressure. Three times the volume of 40% sulfuric acid is added to the concentrated glacial acetic acid solution. Under reflux, the carbamate is boiled to give the free amine. In the course of this, the product precipitates out as the sulfate salt. The salt formed is filtered off and washed with a little cooled ethanol. The resulting solid is dissolved in water/ethanol and the solution is brought to a pH of 9 (nine) with aqueous ammonia solution. At this pH, the free noroxymorphone precipitates out and is filtered off. No α,β-unsaturated by-products are detectable by means of HPLC analysis. Yield: 70-75% (based on the diacetyloxymorphone carbamate used).

HPLC purity: >98%, neither α,β-unsaturated compound nor 3,8,14-triacetyloxymorphone detectable.

What is claimed is:
1. A process for producing noroxymorphone compounds from a crude product, said crude product having been obtained from a plant extract and consisting essentially of noroxymorphone compounds of formula (II), and comprising, as impurities, at least one of the α,β-unsaturated noroxymorphone compounds of the formulae (1a) and (1b),

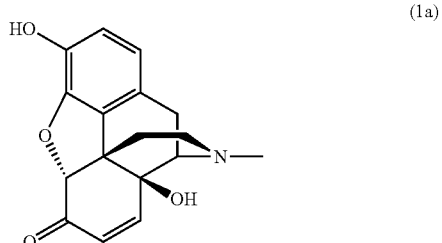

(1a)

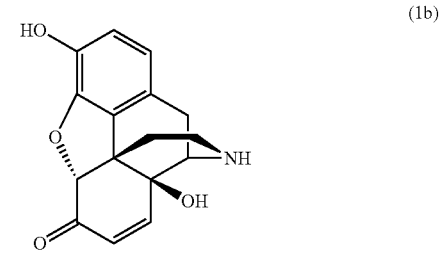

(1b)

wherein said noroxymorphone compounds correspond to the following formula (II):

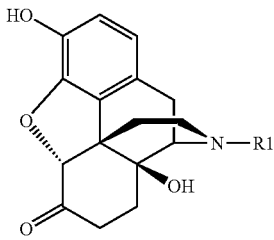

in which
R₁ is hydrogen or methyl as may be contained in the plant extract, or R₁ is a detachable leaving group as subsequently produced synthetically from a natural source, characterized in that:
(a) said crude product is treated in a reaction which converts the hydroxyl groups present in the mixture to leaving groups of the formula —OR₂ in which R₂ is the introduced radical of a leaving group,
(b) these leaving groups are detached,
(c) the resulting mixture is subjected to a selective hydrogenation by which a saturated bond is formed in the α,β-position of the α,β-unsaturated noroxymorphone compounds and any remaining leaving groups are each detached and then,
(d) the pure noroxymorphone compound is isolated.

2. The process as claimed in claim 1, wherein the leaving groups are detached before the selective hydrogenation of step (c).

3. The process as claimed in claim 1, characterized in that the workup of step (a) and of step (b) including the isolation of the reaction products is carried out in a non-aqueous medium.

4. The process as claimed in claim 1, wherein the leaving groups are detached after selective hydrogenation.

5. The process as claimed in claim 1, characterized in that leaving groups still present after the hydrogenation [step (c)] are removed by means of hydrolysis.

6. The process as claimed in claim 1, characterized in that R₁ is hydrogen or methyl.

7. The process as claimed in claim 1, characterized in that R₁ as the leaving group is (C₁-C₄)-alkyloxycarbonyl or phenyloxycarbonyl.

8. The process as claimed in claim 1, characterized in that the leaving group of the formula —OR₂ is an ester moiety.

9. The process as claimed in claim 1, characterized in that —OR₂ is a carbonic ester moiety in which R₂ is (C₁-C₈)-alkyloxycarbonyl or phenyloxycarbonyl.

10. The process as claimed in claim 1, characterized in that R₁ as the leaving group is ethyloxycarbonyl or tert-butyloxycarbonyl (Boc).

11. The process as claimed in claim 1, characterized in that the crude product as a solid contains a total of about at least 70% by weight, of compounds of formula (II) and the ratio of the compounds of the formula (II) to the contaminating noroxymorphone compounds being about in the range from 99.800% by weight to 99.999% by weight.

12. The process as claimed in claim 1, characterized in that the noroxymorphone obtained in stage (a2) is processed further to give naltrexone or naloxone or a salt of these compounds or pharmaceutically acceptable salts of these compounds.

13. The process as claimed in claim 1, characterized in that the noroxymorphone obtained in stage (c) is processed further to give the hydrochloride, hydrobromide, methochloride or methobromide, of naltrexone or naloxone.

14. The process as claimed in claim 1, characterized in that R₁ as the leaving group is (C₁-C₄)-alkyloxycarbonyl or phenylcarbonyl, preferably ethyloxycarbonyl, isobutyloxycarbonyl, or tert-butyloxycarbonyl (Boc), cyclohexyloxy-carbonyl.

15. The process as claimed in claim 1, characterized in that the leaving group of the formula —OR₂ is a formyl ester radical, acetyl ester radical, trichloroacetyl ester radical, trifluoroacetyl ester radical, benzoyl ester radical, optionally substituted benzyl ester groups, i.e. in that R₂ in the —OR₂ radical is formylcarbonyl, methylcarbonyl, trichloromethylcarbonyl, trifluoromethylcarbonyl, phenylcarbonyl, optionally substituted, optionally substituted phenylcarbonyl, or —OR₂ is an ester moiety of a sulfonic acid in which R₂ is methylsulfonyl, benzylsulfonyl or p-toluenesulfonyl.

16. The process as claimed in claim 1, characterized in that —OR₂ is ethyloxycarbonyl, isobutyloxycarbonyl or tert-butyloxycarbonyl (Boc), cyclohexyloxycarbonyl.

17. The process according to claim 1, characterized in that the concentration of the α,β-unsaturated compounds within the pure oxymorphone/noroxymorphone compounds obtained in step (d) is below 10 ppm.

18. The process according to claim 1, characterized in that the concentration of the α,β-unsaturated compounds within the pure oxymorphone/noroxymorphone compounds obtained in step (c) is below 10 ppm.

* * * * *